United States Patent [19]

Matsunaga

[11] Patent Number: 5,476,797
[45] Date of Patent: Dec. 19, 1995

[54] PROCESS AND APPARATUS FOR DETECTING SENSITIZED LEUKOCYTE OR ANTIGEN

[75] Inventor: Tadashi Matsunaga, Fuchu, Japan

[73] Assignee: Asahi DenkaKogyo K.K., Tokyo, Japan

[21] Appl. No.: 135,580

[22] Filed: Oct. 13, 1993

Related U.S. Application Data

[63] Continuation of Ser. No. 599,713, Oct. 19, 1990, abandoned.

[30] Foreign Application Priority Data

Oct. 20, 1989 [JP] Japan ..................................... 1-271566
Oct. 20, 1989 [JP] Japan ..................................... 1-271567

[51] Int. Cl.$^6$ ...................... G01N 33/567; G01N 27/404; G01N 21/64; G01N 27/48
[52] U.S. Cl. ................... 436/513; 422/82.01; 422/82.08; 436/806; 436/808; 204/403
[58] Field of Search ..................................... 436/806, 808, 436/513; 422/82.01, 82.08; 204/403

[56] References Cited

U.S. PATENT DOCUMENTS

| | | | |
|---|---|---|---|
| 3,900,558 | 8/1975 | Kinsoluing | 436/513 |
| 4,216,065 | 8/1980 | Rechnitz et al. | 204/403 |
| 4,543,339 | 9/1985 | O'Neill | 436/510 |
| 4,559,299 | 12/1985 | Rotman | 435/291 |
| 4,559,310 | 12/1985 | Cantor et al. | 436/519 |
| 4,579,642 | 1/1986 | Niiyama et al. | 435/291 |
| 4,734,372 | 3/1988 | Rotman | 422/82.08 |
| 4,780,191 | 10/1988 | Romette et al. | 435/291 |
| 4,920,047 | 8/1990 | Ciaever et al. | 435/7 |
| 4,945,045 | 7/1990 | Forrest et al. | 435/25 |
| 4,999,305 | 3/1991 | Wolcott et al. | 436/52 |

OTHER PUBLICATIONS

Moneret–Vautrin, et al.; Therapie, vol. 33, No. 6, pp. 779–790, 1978.
T. Matsunaga, Cell Technology, vol. 7, No. 6, pp. 472–479, 1988.
Harsing et al., Clin Chem 32:1823–1827 (1986).
White et al., *Fluorescence Analysis*, p. 126 (1970).
Rechnitz et al., Science 199, 440–41 (1978).
Matsunaga, T. "Sensor for Counting Cell Numbers," Saibo Kogaku 7:472–479 (1988) Full Translation.
Matsunaga et al., "Detective of Rat Basophilic Leukemia by Cyclic Voltammetry . . . ," Anal Chem 61:2471–2474 (1989).

*Primary Examiner*—Michael P. Woodward
*Attorney, Agent, or Firm*—Sherman and Shalloway

[57] ABSTRACT

Processes for detecting a sensitized leukocyte or an antigen in a liquid sample are described. One of the processes contains the steps of: adding a known antigen to the liquid sample, or the liquid sample to a known sensitized leukocyte; applying an electric potential between a working electrode immersed in a mixture of the known antigen or the known leukocytes and the liquid sample, and a counter electrode, to generate an electric current therein; and measuring an amount of the electric current generated. Further, another process contains the steps of: adding a known antigen to said liquid sample, or the liquid sample to a known sensitized leukocyte; and measuring an amount of serotonin or histamine released thereby. Still further, apparatuses for carrying out the above processes are also described.

5 Claims, 7 Drawing Sheets

PROCESS AND APPARATUS FOR DETECTING SENSITIZED LEUKOCYTE OR ANTIGEN

This application is a continuation of application Ser. No. 07/599,713, filed Oct. 19, 1990, now abandoned.

BACKGROUND OF THE INVENTION

1. Field of the Invention

The present invention relates to a process and apparatus for detecting a leukocyte sensitized by an antigen, which may be particularly used for identifying an allergen of an allergic patient. Further, the present invention relates to a process and apparatus for detecting an antigen, particularly for simply determining whether or not a particular antigen, and thus, a particular allergen, is present in a particular substance or material.

2. Description of the Related Art

An allergy, such as a pollen allergy, asthma or food allergy, is believed to be caused by an IgE antibody produced in a living body, and as test procedures used to identify an allergen of an allergic patient, the RAST (radioallergosorbent test), ELISA (enzyme-linked immunosorbent assay), Skin prick test, Scratch test, and Elimination and feed test are known.

In a RAST, an IgE antibody is reacted with an immobilized allergen, and then an anti-IgE-antibody labeled with radioactive substances is reacted therewith. Thereafter, the specificity of the IgE antibody of the patient is determined from an amount of radioactivity thereof. Nevertheless, because radioactive substances are used, the RAST requires expensive equipment and complicated procedures, and has a further disadvantage in that the result thereof sometimes does not show an actual allergic symptom, or the like.

In an ELISA test, as in the RAST, an IgE antibody is reacted with an immobilized allergen, and an anti-IgE-antibody labeled with an enzyme is reacted therewith, and thereafter, the specificity of the IgE antibody of the patient is determined from an activity of the enzyme. The ELISA test does not use a radioactive substance, but depends upon an enzymatic reaction, and therefore, may be carried out with simpler equipment than that used in the RAST. Nevertheless, it requires a complicated procedure and prolonged treatment.

The Skin prick test and Scratch test cause pain, because the skin of a patient is scratched to enable the allergen to function.

The elimination and feed test is difficult to complete because the patient must be completely isolated from allergens before the examination. The elimination and feed test also causes pain, because an allergen is administered to enable an allergic symptom to be observed.

A food or drug allergy brings about a tubefaction of or a rash on the skin, because the ingredients in various foods or drugs are absorbed from a digestive organ and act as an allergen. A food or drug allergy is also believed, as for a pollen allergy or the like, to be caused by a participation of an IgE antibody produced against an allergen in a living body.

For these allergic patients, it is important not only to identify the particular allergen specific to the patient, but also to determine whether or not an allergic symptom appears after an intake of a particular food. Unfortunately, however, a simple, accurate and precise process and apparatus for determining whether or not a particular allergen is present in a particular substance or material, such as a food, was hitherto unknown.

SUMMARY OF THE INVENTION

As clear from the above, the development of a process and apparatus which enable the use of a simple procedure, and ensure a high accuracy and precise results is needed when identifying an allergen of an allergic patient, and for determining the presence or absence of an allergen contained in various materials such as a food, and accordingly, an object of the present invention is to provide such a process and apparatus.

Other objects and advantages of the present invention will be apparent from the following description.

Namely, in accordance with the present invention, there is provided a process for detecting a sensitized leukocyte in a liquid sample, comprising the steps of:

adding a known antigen to the liquid sample;

applying an electric potential between a working electrode immersed in a mixture of the antigen and the liquid sample, and a counter electrode, to generate an electric current therein; and measuring an amount of electric current generated.

Further, in accordance with the present invention, there is provided a process for detecting a sensitized leukocyte in a liquid sample, comprising the steps of:

adding a known antigen to the liquid sample; and measuring an amount of serotonin or histamine released thereby.

Still further, in accordance with the present invention, there is provided a process for detecting an antigen in a liquid sample, comprising the steps of:

adding the liquid sample to a known sensitized leukocyte;

applying an electric potential between a working electrode immersed in a mixture of the known sensitized leukocyte and the liquid sample, and a counter electrode, to generate an electric current therein; and measuring an amount of electric current generated.

Still further, in accordance with the present invention, there is provided a process for detecting an antigen in a liquid sample, comprising the steps of:

adding the liquid sample to a known sensitized leukocyte; and measuring an amount of serotonin or histamine released thereby.

Still further, in accordance with the present invention, there is provided an apparatus for detecting an antigen in a liquid sample, comprising:

an electrode carrying a sensitized leukocyte;

a means for carrying out voltammetry, this means containing the electrode;

a reaction chamber wherein a type I allergic reaction is carried out, this chamber containing the electrode; and a means for injecting the liquid sample to the chamber.

Still further, in accordance with the present invention, there is provided an apparatus for detecting a sensitized leukocyte in a liquid sample or an antigen in a liquid sample, comprising:

a reaction chamber containing the liquid sample or a known sensitized leukocyte, wherein a type I allergic reaction is carried out;

a means for injecting an antigen as a reference, or the liquid sample, to the chamber; and a means for carrying out voltammetry to thereby detect a peak current of serotonin released by the type I allergic reaction in the reaction chamber.

Still further, in accordance with the present invention, there is provided an apparatus for detecting a sensitized leukocyte in a liquid sample or an antigen in a liquid sample, comprising:

a reaction chamber containing the liquid sample or a known sensitized leukocyte, wherein a type I allergic reaction is carried out;

a means for injecting an antigen as a reference, or the liquid sample, to the chamber; and a means for measuring a fluorescence of serotonin released by the type I allergic reaction in the reaction chamber.

Still further, in accordance with the present invention, there is provided an apparatus for detecting a sensitized leukocyte in a liquid sample or an antigen in a liquid sample, comprising:

a first reaction chamber including the liquid sample or a known sensitized leukocyte, wherein a type I allergic reaction is carried out;

a means for injecting an antigen as a reference, or the liquid sample, to the first reaction chamber;

a second reaction chamber wherein a deamination of histamine produced by the type I allergic reaction in the first reaction chamber is carried out in the presence of diamineoxidase; and a means for directly or indirectly detecting a product of the deamination in the second reaction chamber.

DESCRIPTION OF THE PREFERRED EMBODIMENTS

Detection of Sensitized Leukocyte

Figure 1:
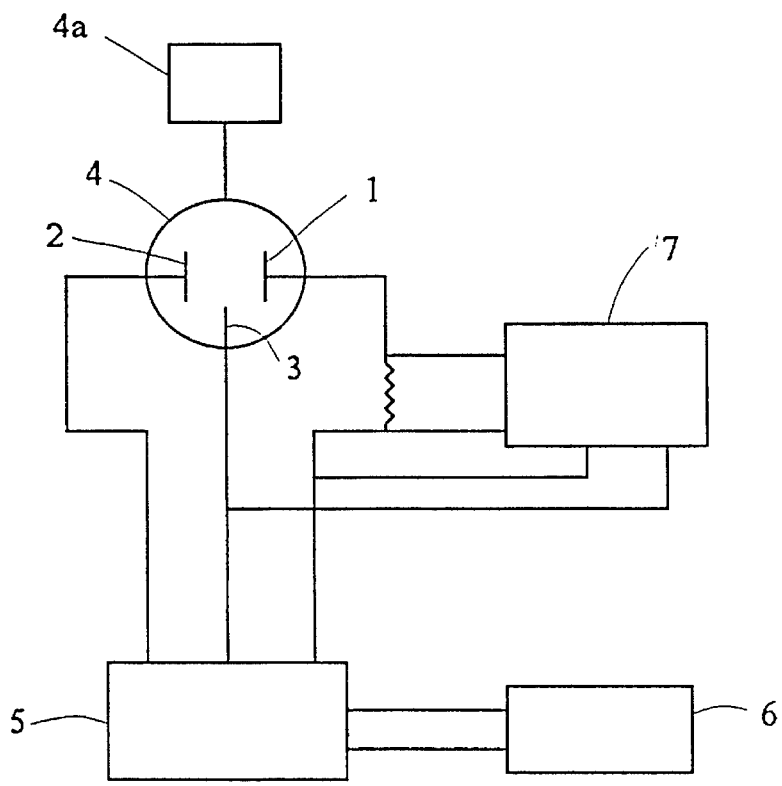
FIG. 1 schematically illustrates an example of an apparatus for cyclic voltammetry to carry out a first embodiment of the present invention.

According to the present invention, it is possible to determine whether or not a leukocyte included in the blood of a mammal (in particular, a human being) is sensitized with an antigen (in particular, an allergen), and thus exactly identify the allergen of the mammal (in particular, the human being).

The "liquid sample" (optionally referred to as a "leukocyte sample" hereinafter) used in the present invention for the detection of a leukocyte is a liquid which is an object of the detection, and possibly contains a leukocyte sensitized with an antigen, in particular, with an allergen. In the present specification, the term "leukocyte" means all hemocytes (blood cells) in whole blood other than erythrocytes (red blood cells) and platelets, and thus includes neutrophils, eosinophils, basophils, lymphocytes, and monocytes, or the like. Generally, cells relating to the type I allergy are said to be a mast cell, basophil and eosinophil carrying IgE antibody receptors on the surfaces thereof. In the detection of the present invention, however, it is not necessary to separate only the basophil and eosinophil from the leukocytes in the leukocyte sample.

A preferable leukocyte sample is prepared by separating leukocytes from the serum of a mammal (in particular, a human being) by centrifugation or the like, and then diluting the leukocytes with a physiological saline. It is important to ensure the survival of the leukocyte in the leukocyte sample, and thus the leukocyte sample is preferably isotonic to blood. At the same time, preferably the leukocyte sample has a buffer function. In particular, if an electrode method or an enzymatic method (mentioned below, respectively) is carried out, the buffer function is required for the leukocyte sample because variations of the pH values of the leukocyte sample cause unstable current values, or a reduction of the enzymatic activity. Therefore, it is more preferable to use a buffer which is isotonic to blood, and at the same time, has a buffer function, for example, a PBS (phosphate buffered saline), or a Hank's buffer.

In this aspect of the present invention, the type I allergic reaction is caused by adding a known antigen to the liquid sample, i.e., the leukocyte sample. In the present specification, the term "known" means that the "known" antigen to be added is used as a standard or a reference for identifying an antigen with which the leukocytes included in the leukocyte sample are sensitized. It is sufficient that the origin of the antigen is known or clear to the extent that the antigen makes it possible to identify an unknown antigen with which the leukocytes included in the leukocyte sample taken from an object (for example, a patient) are sensitized, when the leukocytes are sensitized, or to the extent that the antigen makes it possible to determine that the leukocytes are not sensitized by the "known" antigen or are sensitized by other unknown antigen. It is not necessary for the composition or structure of the "known" antigen per se to be known or clear from a chemical standpoint of view. Further, it is not necessary that the "known" antigen to be added is a previously known allergen capable of causing an allergy. On the other hand, the term "unknown" used herein means that the "unknown" antigen is an object of the detection, i.e., the kind and/or presence of the "unknown" antigen is unclear prior to the detection performed in accordance with the present invention, and the term "unknown" does not mean that the "unknown" antigen substance per se is novel.

Examples of the antigen, in particular, the allergen, are food, such as cow's milk, hen's eggs, soybeans, lobsters, shrimps, prawns, mackerel, bamboo shoots, or soba (Japanese noodle); pollen, such as the pollen of a Japanese cedar (sugi), a rice plant or ragweed; medicines such as vaccines or penicillin; fur, such as the fur of a dog or cat; a tick, such as Dermatophagoides farinae or Dermatophagoides pteronyssinus; an insect such as a midge; mold such as Candida; a fiber material such as silk; or dust in a room. A liquid allergen may be used as is without treatment, or if necessary, after a dilution or extraction by an appropriate solvent such as water, a physiological saline or a buffer. A solid allergen is used after a dilution or extraction by an appropriate solvent such as water, a physiological saline or a buffer.

An allergen containing an extract or dilute preferably contains the allergen in an amount of 1 ng/ml or more, more preferably 1 µg/ml or more, with respect to a protein amount, but is not limited thereto.

Detection of Antigen

In a second aspect of the present invention, it is possible to determine whether or not a particular antigen (notably, a particular allergen) is contained in various materials which may be taken in and/or touched by a mammal (in particular, a human being).

The various materials, i.e., a liquid sample (optionally referred to as an "antigen sample" hereinafter) which is an object of the detection according to the second aspect of the present invention, are not limited, as long as they are taken in and/or touched by a mammal (in particular, a human being). Examples thereof are food, such as cow's milk, hen's eggs, soybeans, lobsters, shrimps, sprawn, mackerel, bamboo shoots, or soba (Japanese noodle); processed foodstuffs thereof such as confectionary (e.g., biscuits or rice crackers), a main article (e.g., bread or pilaf), an article for a daily dish (e.g., hamburger, curry soup, or a stew) or a seasoning [e.g., soy sauce (shoyu) or miso ]; non-allergen processed foodstuffs (e.g., the above processed foodstuffs) prepared so as to remove one or more particular allergens (e.g., cow's milk, hen's eggs, soybeans, lobsters, shrimps, prawns, mackerel, bamboo shoots, or soba , as above); pollen, such as the pollen of a Japanese cedar (sugi), a rice plant or ragweed; medicines such as vaccines or penicillin; fur, such as the fur of a dog or cat; a tick, such as Dermatophagoides farinae or Dermatophagoides pteronyssinus; an insect such as a midge; mold such as Candida; a fiber material such as silk; or dust in a room. A liquid material containing the antigen (particularly, the allergen) may be used as the antigen sample without a treatment, or if necessary, after a dilution or extraction by an appropriate solvent such as water, a physiological saline or a buffer. A solid material containing the antigen (particularly, the allergen) is used as the antigen sample after a dilution or extraction by an appropriate solvent such as water, a physiological saline, or a buffer.

In this aspect of the present invention, an antigen (in particular, an allergen) in a liquid sample, which antigen is an object of the detection is identified, using a sensitized leukocyte (optionally referred to as a "sensitized reference leukocyte" hereinafter) as a reference material. The kind and/or origin of the antigen (in particular, the allergen) contained in a liquid sample is unknown, prior to the detection of the present invention. The sensitized reference leukocyte used in this aspect of the present invention includes leukocytes containing basophils, eosinophils or the like sensitized with one or more particular antigens, and makes it possible to determine the presence of one or more particular antigens in the liquid sample. It is not necessary that a composition, structure or the like of the sensitized reference leukocyte or IgE antibody per se be known from a chemical standpoint of view. The sensitized reference leukocyte or IgE antibody used is not limited to those sensitized with conventionally known antigens. Further, when the kind of the particular antigen with which the leukocyte is sensitized is clear, not only the presence but also the kind of the antigen contained in the liquid sample can be identified.

In this aspect of the present invention, the term "leukocyte" also means all hemocytes (blood cells) in whole blood other than erythrocytes (red blood cells) and platelets, and thus includes neutrophils, eosinophils, basophils, lymphocytes, monocytes, or the like, respectively or in the form of a mixture thereof. Generally, cells relating to the type I allergy are said to be a basophil and eosinophil carrying IgE antibody receptors on the surfaces thereof. Therefore, this aspect of the present invention may be carried out using only basophils and/or eosinophils. It is also possible to use whole leukocytes without separating only the basophils and/or eosinophils therefrom.

The sensitized reference leukocyte used in the present invention may be prepared by various methods.

For example, leukocytes may be taken from a mammal (particularly, a human being, monkey, rat, mouse, rabbit, horse or goat) which is known to have been sensitized with one or more particular antigens, or which has been sensitized with one or more particular antigens. In this case, it is preferable to use the taken whole leukocytes, without separating basophils and/or eosinophils therefrom. Whether the leukocyte is sensitized with one or more particular antigens can be determined by, for example, the RAST, ELISA test, Skin prick test, Scratch test, and the elimination and feed test, or further, by the above-mentioned aspect of the present invention described in the section "Detection of Sensitized Leukocyte". Further, a mammal may be sensitized with one or more particular antigens by means of, for example, an oral administration, or an intravenous or intraperitoneal injection.

Leukocytes, particularly basophils and/or eosinophils, may be cultivated, and the resulting cultivated leukocytes then sensitized with one or more particular IgE antibodies in vitro. The cultivation of the basophils and/or eosinophils may be carried out by conventional methods. The IgE antibody may be a polyclonal antibody prepared from antiserum, or a monoclonal antibody prepared by a cell fusion technique. The cultivated leukocytes sensitized with one or more particular IgE antibody may be prepared by incubating the cultivated cells and the IgE antibodies in appropriate conditions, whereby the particular IgE antibodies are bonded to the IgE antibody-receptor on the cultivated cells. Further, in this method, an IgE antibody of a particular animal (i.e., one of the above-mentioned mammals) may be bonded to the IgE antibody-receptor on the cultivated leukocytes of a different animal. The cultivated leukocyte sensitized as above can be used in the present invention. A complicated procedure usually required when separating a sensitized human leukocyte from human blood can be eliminated, by carrying out the detection of the present invention using, for example, a cultivated rat leukocyte sensitized with a human antiserum in accordance with the above method. Further, unlike a leukocyte, an antiserum can be stored when frozen, and therefore, a detection using an antiserumdoes not require a fresh preparation of the antiserum for each detection. Accordingly, the detection of the present invention can be steadily carried out whenever a cultivated leukocyte is supplied. In this specification, the type I allergic reaction means a reaction wherein antigens are bonded to corresponding IgE antibodies on sensitized basophils and/or sensitized eosinophils, and the antibodies are bridged by the antigens, whereby a degranulation is caused, and then chemical mediators, such as serotonin or histamine, are released or liberated to the outside of a cell.

Various embodiments of the present invention will be described hereinafter.

First Embodiment

A first embodiment of the present invention utilizes a voltammetry technique, such as differential pulse polarograph, phase difference alternative current polarograph, or square wave polarograph, and although various apparatuses for voltammetry can be used, the first embodiment will be explained hereinafter with reference to an apparatus for cyclic voltammetry.

FIG. 1 schematically illustrates an example of an apparatus for cyclic voltammetry. The apparatus mainly comprises an electrode carrying a leukocyte sample or a sensitized reference leukocyte, a voltammetry measuring means containing the electrode, a reaction chamber containing the electrode wherein the type I allergic reaction is carried out, and an injecting means for supplying to the chamber a reference antigen (to the leukocyte sample on the electrode), or an antigen sample (to the sensitized reference leukocyte on the electrode). Namely, the apparatus comprises mainly a reaction detecting system and a recording system. The reaction detecting system comprises an electrolytic cell 4 comprising a working electrode 1, a counter electrode 2, and a reference electrode 3. The recording system comprises a potentiostat 5, scanning or sweep electric source 6, and an XY recorder or synchroscope 7, etc.

The voltammetry measuring means comprises electrodes (the working electrode 1, the counter electrode 2, and the reference electrode 3), the potentiostat 5, scanning or sweep electric source 6, and the XY recorder or synchroscope 7, etc. An electrode made of platinum, gold, silver, stainless steel, carbon or a conductive polymeric material, or preferably various modified electrodes coated with a conductive polymeric material, may be used as the electrode 1 or 2. As examples of the reference electrode 3 which may be used, an SCE (saturated calomel electrode), an SSCE (saturated sodium chloride calomel electrode), and a silver/silver chloride electrode may be mentioned. When a potential of the counter electrode 2 is stable and constant, the reference electrode 3 may be eliminated, i.e., a circuit structure of a conventional polarograph can be used.

Figure 2:
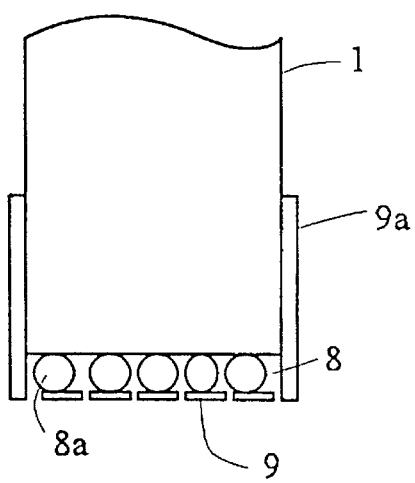
FIG. 2 is a sectional view showing a state wherein a carrier for supporting leukocytes is brought into contact with and fixed to a working electrode in the apparatus of FIG. 1.
Figure 3:
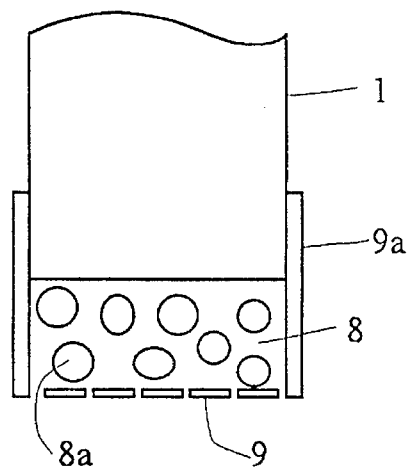
FIG. 3 is a sectional view showing a state wherein a carrier for supporting leukocytes is arranged near a working electrode in the apparatus of FIG. 1.

When the detection of the leukocyte in a liquid sample according to the first aspect of the present invention is carried out, the leukocyte sample per se may be injected as an electrolyte, if a concentration of the leukocytes in the liquid sample is very high ($10^5$ cells/μl or more). Preferably, an electrolyte, such as a physiological saline, is injected into the electrolytic cell 4, and thereafter, the leukocyte sample 8 is immobilized on an appropriate carrier 9 (for example, a membrane filter or dialysis membrane having a pore size of 25 nm to 10 μm), and the working electrode 1 and the carrier 9 are brought into contact with each other and fixed by an appropriate fixing means 9a, whereby the leukocytes 8a are brought into firm contact with the working electrode 1 (FIG. 2). Alternatively, the carrier 9 is disposed near the working electrode 1 by the appropriate fixing means 9a, and the liquid sample 8 containing leukocytes 8a is trapped in a narrow space between the carrier 9 and the working electrode 1, whereby a high concentration of the leukocytes 8a in the liquid sample 8 around the working electrode 1 is assured (Fig.3).

The leukocyte sample can be immobilized on the carrier 9 by injecting the liquid sample (leukocyte sample) 8 to the carrier 9 in the side of the electrode 1, by dipping the carrier 9 in the liquid sample 8 containing leukocytes 8a and then removing same therefrom, or by applying or spraying the liquid sample to the carrier 9.

The number of leukocytes on the carrier 9 is not limited, but preferably the number of leukocytes brought into contact with the working electrode 1 is $10^2$ or more, more preferably, $10^5$ or more. When the number of leukocytes is small, an amplifier or the like must be used. The increase of the number of leukocytes brought into contact with the working electrode 1 generally brings about an increase of the current value, and thus makes the detection easier. Nevertheless, the maximum number of leukocytes which can be brought into direct contact with the working electrode 1 depends on the surface area thereof available for this contact with the leukocytes. Namely, if the number of leukocytes is greater than a certain value, some leukocytes will overlap each other and cannot be brought into direct contact with the electrode surface, and thus no increase of the current value occurs. The maximum number of leukocytes (per a unit area) which can be brought into contact therewith, although differing from one animal to another, is generally about $10^4$ to $10^6$ cells/mm$^2$.

After the leukocyte sample is brought into contact with the working electrode 1, a periodically scanning (sweep) potential is applied between the electrodes to generate an electric current, and the generated current is measured. As the potential scanning, a linear scanning wherein a potential is changed in proportion with time is preferably used. For the leukocyte on the carrier 9, a peak current is preferably obtained at 0.24 V to 0.44 V.vs.SCE, more preferably at 0.29 V to 0.39 V.vs.SCE, and the measured peak current is recorded.

Thereafter, various reference antigens (particularly, allergens) are added to the electrolytic cell 4, and a periodical scanning potential is applied between the electrodes, respectively, as described above. When the leukocytes in the liquid sample are not sensitized with an antigen, or are sensitized with an antigen other than that added to the electrolytic cell 4, the peak current appearing at 0.24 V. to 0.44 V.vs.SCE, preferably at 0.29 V. to 0.39 V.vs.SCE does not change. Nevertheless, if an unknown antigen with which the leukocytes in the liquid sample are sensitized is identical to the known antigen added to the electrolytic cell 4, the above peak current is reduced. Accordingly, it is possible to determine the kind of the antigen with which the leukocytes in the liquid sample are sensitized.

When the detection of the antigen according to the second aspect of the present invention is carried out, the sensitized reference leukocyte is supported on the working electrode 1. Preferably, as shown in FIGS. 2 and 3, sensitized reference leukocytes 8a in the liquid 8 are immobilized on an appropriate carrier 9 (for example, a membrane filter or dialysis membrane having a pore size of 25 nm to 10 μm), and the working electrode 1 and the carrier 9 are brought into contact with each other and fixed by an appropriate fixing means 9a, whereby the reference leukocytes 8a are brought into firm contact with the working electrode 1 (FIG. 2). Alternatively, the carrier 9 is disposed near the working electrode 1 by the appropriate fixing means 9a, and the liquid 8 containing sensitized reference leukocytes 8a is trapped in a narrow space between the carrier 9 and the working electrode 1, whereby a high concentration of the reference leukocytes 8a in the liquid 8 around the working electrode 1 is assured (FIG. 3).

The sensitized reference leukocytes 8 can be immobilized on the carrier 9 by injecting the liquid 8 containing sensitized reference leukocytes 8a to the carrier 9 in the side of the electrode 1, by dipping the carrier 9 in the liquid 8 containing sensitized reference leukocytes 8a and then removing same therefrom, or by applying or spraying the sensitized reference leukocytes to the carrier 9. The number of sensitized reference leukocytes on the carrier 9 is not limited, but preferably the number of the sensitized reference leukocytes brought into contact with the working electrode 1 is $10^2$ or more, more preferably, $10^5$ or more. When the number of the leukocytes is small, an amplifier or the like must be used.

The type I allergic reaction is carried out in a reaction chamber, i.e., the electrolytic cell 4 comprising the electrodes 1 to 3. This electrolytic cell 4 is provided with an injecting means for supplying an antigen sample, for example, an injector 4a.

The detection using this apparatus may be started by supplying an electrolyte, such as a physiological saline or a buffer, from the injector 4a to the electrolytic cell 4, and measuring an electric current generated upon applying a periodically scanning (sweep) potential between the electrodes, before supplying an antigen sample from the injector 4a. As the potential scanning, a linear scanning wherein a potential is changed in proportion with time is preferably used. For the reference leukocyte on the carrier 9, a peak current is preferably obtained at 0.24 V to 0.44 V.vs.SCE, more preferably at 0.29 V to 0.39 V.vs.SCE, and the measured peak current is recorded.

Thereafter, various liquid samples containing unknown antigens (particularly, allergens) are supplied from the injector 4a to the electrolytic cell 4, and a periodical scanning potential is applied between the electrodes, as described above.

When an antigen capable of bonding to IgE antibodies on the sensitized reference leukocytes is not present in the liquid sample (antigen sample), the peak current appearing at 0.24 V. to 0.44 V.vs.SCE, preferably at 0.29 V. to 0.39 V.vs. SCE does not change. Nevertheless, if an antigen capable of bonding to IgE antibodies on the sensitized leukocytes is present in the liquid sample (antigen sample), the above peak current is reduced. The degree of the reduction of the peak current is proportional to the amount of antigen. Therefore, as described above, it is possible to detect, in the liquid sample (antigen sample), the presence and absence of an antigen which is the same as the known antigen with which the reference leukocytes are sensitized.

In both the detection of the leukocyte and of the antigen, several milimoles to about one hundred milimoles of 4,4'-bipyridine are preferably contained in the electrolytic cell 4, because a considerably large reduction of the peak current is thus obtained. Alternatively, 4,4'-bipyridine may be impregnated in the carrier.

Figure 4:
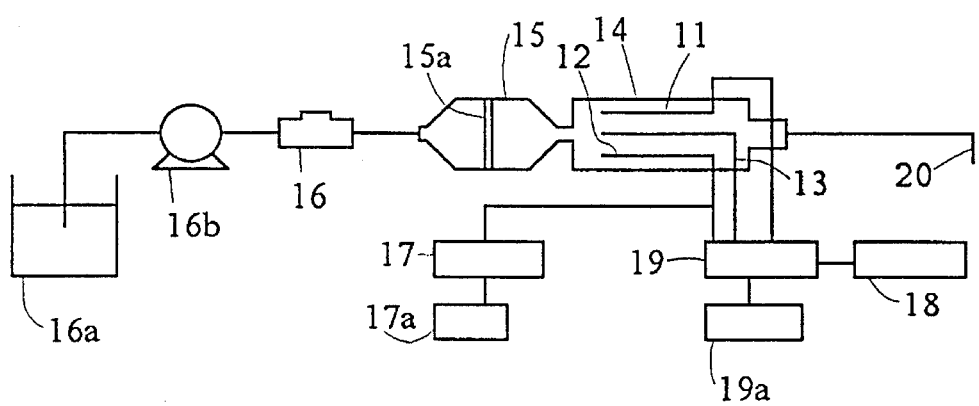
FIG. 4 schematically illustrates an example of an apparatus for cyclic voltammetry in a continuous manner to carry out a second embodiment of the present invention.

Although the batch process is described for the first embodiment of the present invention as above, this embodiment can be carried out in a continuous manner, using an apparatus as shown in FIG. 4, wherein a reaction chamber 15 and a carrier membrane 15a supporting the leukocytes are omitted from the apparatus shown in FIG. 4, and the carrier 9 is brought into contact with the working electrode 1, whereby the type I allergic reaction is carried out in the electrolytic cell 4.

The reason why the presence of the leukocyte sensitized with a particular allergen in a liquid sample, or the presence of a particular allergen in a liquid sample can be detected according to the first embodiment of the present invention is assumed to be as follows, although the present invention is not limited to the following assumption:

It is known that, when a living cell touches an electrode an electric current is generated, and a cyclic voltammetry technique may be applied to the electrode reaction to obtain a peak current. In the first embodiment of the present invention, accordingly, it is assumed that, when an allergen is bonded to leukocytes sensitized with IgE antibodies and brought into contact with an electrode, chemical mediators are released from the sensitized leukocytes and a peak current is reduced upon this release, whereby the detection can be carried out.

Second Embodiment

According to a second embodiment of the present invention, a measurement is made of serotonin, which is a chemical mediator released upon a bonding of an allergen to leukocytes sensitized therewith, and the serotonin may be measured by a voltammetry technique. This embodiment will be optionally referred to as a "serotonin electrode technique" hereinafter. Further, the serotonin emits fluorescence at 325 to 335 nm, particularly 330 nm, when exposed to an exciting wave length of 293 to 303 nm, particularly 298 nm, and therefore, a measurement can be made by utilizing this fluorecenece. This embodiment will be optionally referred to as a "serotonin fluorescence technique" hereinafter.

Serotonin Electrode Technique

As in the first embodiment of the present invention, the serotonin electrode technique utilizes a voltammetry technique, such as differential pulse polarograph, phase difference polarograph, square wave polarograph, and although various apparatuses for voltammetry can be used, the serotonin electrode technique will be explained hereinafter with reference to an apparatus for cyclic voltammetry.

FIG. 4 schematically illustrates an example of an apparatus for cyclic voltammetry in a continuous manner. The apparatus mainly comprises a detecting system containing an electrolytic cell 14 having electrodes, etc.; a reaction system containing a reaction chamber 15 having a leukocyte carrying membrane 15a, etc.; an injecting system containing an injector 16, a buffer reservoir 16a, a pump 16b, etc.; and a measuring and recording system containing a microammeter 17, a current recorder 17a, a function generator 18, a potentiostat 19, and a potential recorder 19a, etc. The voltammetry measuring means comprises the detecting system and the measuring and recording system. The electrodes in the electrolytic cell 14 include a working electrode 11, a counter electrode 12, and a reference electrode 13. As in the apparatus as shown in FIG. 1, an electrode made of platinum, gold, silver, stainless steel, carbon or a conductive polymeric material, or preferably various modified electrodes coated with a conductive polymeric material, may be used as the electrode 11 or 12. As examples of the reference electrode 13 which may be used, an SCE (saturated calomel electrode), an SSCE (saturated sodium chloride calomel electrode), and a silver/silver chloride electrode may be mentioned. When a potential of the counter electrode 12 is stable and constant the reference electrode 13 may be eliminated, i.e., a circuit structure of a conventional polarograph can be used.

When the detection of the leukocyte according to the first aspect of the present invention is carried out, a buffer is supplied from the buffer reservoir 16a by the pump 16b to the reaction chamber 15 and the electrolytic cell 14, and thereafter discharged from a drainage conduit 20, and thus the measuring system is made stable.

Thereafter, leukocytes contained in the leukocyte sample are immobilized on the membrane 15a (for example, a membrane filter or dialysis membrane having a pore size of 25 nm to 10 μn) used for carrying leukocytes in the reaction chamber 15.

The immobilization can be carried out by injecting the leukocyte sample through the injector 16 into the system, to thereby immobilize the leukocytes on the membrane 15a, or by inserting into the reaction chamber 15a membrane 15a on which leukocytes in the leukocyte sample have been immobilized. Leukocytes may be immobilized on the membrane 15a by dipping the membrane 15a in the liquid sample (leukocyte sample), and then removing same therefrom, or by applying or spraying the liquid sample (leukocyte sample) to the membrane 15a.

The number of leukocytes on the membrane 15a is not limited, but is preferably, $10^2$ or more, more preferably, $10^5$ or more. When the number of leukocytes is small, an amplifier or the like must be used.

Thereafter, a liquid containing a reference antigen (particularly, allergen) is supplied from the injector 16. The supply rate is not limited but is preferably 1.0 ml/min. or less.

After supplying the liquid containing the reference antigen, a periodical scanning (sweep) potential is applied between the electrodes, and the generated current is measured. As the potential scanning, a linear scanning wherein a potential is changed in proportion with time is preferably used.

When the leukocytes in the liquid sample are not sensitized with a reference antigen, or are sensitized with an antigen other than the reference antigen added from the injector 16, the peak current does not change, or a peak current is not observed. Nevertheless, if an unknown antigen with which the leukocytes in the liquid sample are sensitized is identical to the known reference antigen added, the peak current is increased. Accordingly, it is possible to determine the kind of the antigen with which the leukocytes in the liquid sample are sensitized.

When an examination of one of reference antigens is completed, the injection thereof is stopped, the system is washed by the buffer from the buffer reservoir 16a, and then a liquid containing a next reference antigen is injected.

When the detection of the antigen according to the second aspect of the present invention is carried out, sensitized reference leukocytes are immobilized on the membrane 15a (for example, a membrane filter or dialysis membrane having a pore size of 25 nm to 10 μm) used for carrying leukocytes in the reaction chamber 15. The immobilization can be carried out by injecting a liquid containing the sensitized reference leukocytes through the injector 16 into the system, to thereby immobilize the leukocytes on the membrane 15a, or by inserting a membrane 15a on which the sensitized reference leukocytes have been immobilized into the reaction chamber 15. When the liquid containing the sensitized reference leukocytes is supplied from the injector 16, a leukocyte suspension wherein the number of the leukocytes is adjusted is supplied by a microsyringe or the like.

Reference leukocytes may be immobilized on the membrane 15a by dipping the membrane 15a in the liquid containing the sensitized reference leukocytes, and then removing same therefrom, or by applying or spraying the liquid containing the sensitized reference leukocytes to the membrane 15a.

The number of leukocytes on the membrane 15a is not limited, but is preferably, $10^2$ or more, more preferably, $10^5$ or more. When the number of leukocytes is small, an amplifier or the like must be used.

Instead of immobilization on the membrane 15a, a liquid containing the reference leukocytes may be present in the reaction chamber 15. In this case, it is preferable to arrange, between the reaction chamber 15 and the electrolytic cell 14, a membrane (for example, a membrane filter) which permits serotonin, but not leukocytes, to pass therethrough.

When the detection of the antigen according to the second aspect of the present invention is carried out, a buffer is supplied from the buffer reservoir 16a by the pump 16b to the reaction chamber 15 and the electrolytic cell 14, and thereafter discharged from a drainage conduit 20, and thus the measuring system is made stable.

Then, a liquid sample containing an antigen (particularly, allergen) is supplied from the injector 16, and after the antigen sample is supplied, a periodical scanning (sweep) potential is applied between the electrodes, and a generated current is measured. As the potential scanning, a linear scanning wherein a potential is changed in proportion with time is preferably used.

When an antigen capable of bonding to IgE antibodies on the sensitized reference leukocytes is not present in the liquid sample (antigen sample), the peak current appearing at 0.24 V. to 0.44 V.vs.SCE, preferably at 0.29 V. to 0.39 V.vs.SCE does not change, or the peak current is not observed. Further, if an antigen capable of bonding to IgE antibodies on the sensitized leukocytes is present in the liquid sample (antigen sample), the above peak current is increased, and the degree of the increase of the peak current is proportional to the amount of antigen. Therefore, as described above, it is possible to detect, in the liquid sample (antigen sample), the presence and absence of an antigen which is the same as the known antigen with which the reference leukocytes are sensitized.

When an examination of one of antigen samples is completed, the injection thereof is stopped, the system is washed by the buffer from the buffer reservoir 16a, and then a next antigen sample is injected.

In both the detection of the leukocyte and of antigen, several milimoles to about one hundred milimoles of 4,4'-bipyridine are preferably contained in the measuring system, because a considerably large increase of the peak current is thereby obtained. The 4,4'-bipyridine may be supplied in the system from the buffer reservoir 16a.

Although the continuous process is described for the serotonin electrode technique explained above, this embodiment can be carried out batchwise using the same apparatus as that shown in FIG. 1, except that the electrodes are not brought into contact with leukocytes but only with serotonin released by the type I allergic reaction.

Serotonin Fluorescence Technique

Although various apparatuses for fluorometry can be used, the serotonin fluorescence technique will be explained with respect to the use of a fluorescence-spectrophotometer.

Figure 5:
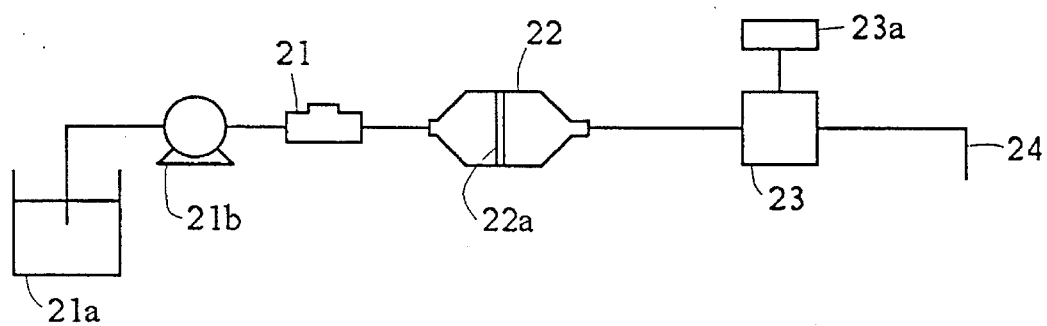
FIG. 5 schematically illustrates an example of an apparatus for fluorimetry in a continuous manner to carry out a second embodiment of the present invention.

FIG. 5 schematically illustrates an example of an apparatus used for a continuous process. The apparatus mainly comprises an injecting system containing an injector 21, a buffer reservoir 21a, and a pump 21b, etc.; a reaction system containing a reaction chamber 22 having a leukocyte carrying membrane 22a, etc.; and a measuring and recording system containing a fluorescence-spectrophotometer 23 and an integrator 23a, etc.

The detection of the leukocyte by the serotonin fluorescence method according to the first aspect of the present invention may be performed in the same way as in the serotonin electrode method. Namely, a buffer is supplied from the buffer reservoir 21a to the reaction chamber 22, and thereafter, discharged from a drainage conduit 24, and thus the measuring system is made stable. Thereafter, leukocytes contained in the leukocyte sample are immobilized on the membrane 22a (for example, a membrane filter or dialysis membrane having a pore size of 25 nm to 10 μm) used for carrying leukocytes in the reaction chamber 22.

The immobilization can be carried out, as in the serotonin electrode technique, by injecting the leukocyte sample from the injector 21 into the system to thereby immobilize the leukocytes on the membrane 22a, or by inserting into the reaction chamber 22a membrane 22a on which leukocytes in the leukocyte sample have been immobilized.

The number of leukocytes on the membrane 22a is not limited, but is preferably $10^2$ or more, more preferably $10^5$ or more. When the number of leukocytes is small, an amplifier or the like must be used.

Then, a liquid containing a reference antigen (particularly, allergen) is supplied from the injector 21. The supply flow rate is not limited, but is preferably 1.0 ml/min. or less.

After supplying the liquid containing the reference antigen, an exciting wave length (293 to 303 nm, particularly 298 nm) is applied to the liquid sent to the fluorescencespectrophotometer 23 to generate a fluorescence at 325 to 335 nm, particularly 330 nm, and an amount of generated fluorescence is measured.

When the leukocytes in the liquid sample are not sensitized with a reference antigen, or are sensitized with an antigen other than the reference antigen added from the injector 21, the fluorescence is not observed. Nevertheless, if an unknown antigen with which the leukocytes in the liquid sample are sensitized is identical to the known reference antigen added, the fluorescence emitted from serotonin is observed. Accordingly, it is possible to determine the kind of the antigen with which the leukocytes in the liquid sample are sensitized.

When an examination of one of the reference antigens is completed, the injection thereof is stopped, the system is washed by the buffer from the buffer reservoir 21a, and then a liquid containing a next reference antigen is injected.

When the detection of the antigen according to the second aspect of the present invention is carried out, sensitized reference leukocytes are immobilized on the membrane 22a (for example, a membrane filter or dialysis membrane having a pore size of 25 nm to 10 μm) used for carrying leukocytes in the reaction chamber 22. The immobilization can be carried out, as in the serotonin electrode technique, by injecting a liquid containing the sensitized reference leukocytes from the injector 21 into the system to thereby immobilize the leukocytes on the membrane 22a, or by inserting into the reaction chamber 22 a membrane 22a on which the sensitized reference leukocytes have been immobilized.

The number of leukocytes on the membrane 22a is not limited, but is preferably 102 or more, more preferably $10^5$ or more. When the number of leukocytes is small, an amplifier or the like must be used.

Instead of immobilizing the reference leukocytes on the membrane 22a, a liquid containing the reference leukocytes may be present in the reaction chamber 22. In this case, it is preferable to arrange, between the reaction chamber 22 and the fluorescence-spectrophotometer 23, a membrane (for example, a membrane filter) which permits serotonin, but not leukocytes, to pass therethrough.

The detection of the antigen according to the second aspect of the present invention is carried out in the same manner as in the serotonin electrode technique. Namely, the whole system is made stable by the buffer supplied from the buffer reservoir 21a, and a liquid sample containing an antigen (particularly, an allergen) is then supplied from the injector 21.

After supplying the antigen sample, an exciting wave length (293 to 303 nm, particularly 298 nm) is applied to the sample sent to the fluorescence-spectrophotometer 23 to generate a fluorescence at 325 to 335 nm, particularly at 330 nm, and an amount of generated fluorescence is measured.

When an antigen capable of bonding to IgE antibodies on the sensitized reference leukocytes is not present in the liquid sample (antigen sample), a fluorescence at 325 to 335 nm is not observed. On the other hand, a fluorescence at 325 to 335 nm is observed, if an antigen capable of bonding to IgE antibodies on the sensitized leukocytes is present in the liquid sample (antigen sample). An amount of the fluorescence is proportional to that of the antigen. Therefore, as described above, it is possible to detect, in the liquid sample (antigen sample), the presence and absence of an antigen which is the same as the known antigen with which the reference leukocytes are sensitized.

When an examination of one of antigen samples is completed, the injection thereof is stopped, the system is washed by the buffer from the buffer reservoir 21a, and then a next antigen sample is injected.

Although the continuous process is described, this embodiment of the serotonin fluorescence technique can be carried out batchwise. In the batch process, preferably only serotonin released from the type I allergic reaction is sent to a fluorescence-spectrophotometer, instead of sending leukocytes thereto.

Third Embodiment

According to a third embodiment of the present invention, a measurement is made of the amount of histamine, which is a chemical mediator released upon a bonding of an antigen (in particular, an allergen) to leukocytes sensitized therewith. A deamination of histamine is caused by diamineoxidase, whereby ammonia or hydrogen peroxide is generated. Therefore, the histamine content can be measured by measuring the amount of ammonia or hydrogen peroxide generated. This embodiment will be optionally referred to as an "enzymatic technique" hereinafter.

Enzymatic Technique

In the presence of diamineoxidase, histamine is reacted as follows:

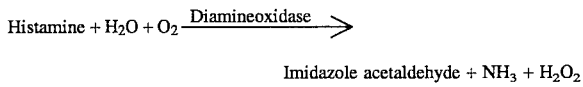

Imidazole acetaldehyde + NH$_3$ + H$_2$O$_2$

Accordingly, the above ammonia or hydrogen peroxide can be detected directly or after a conversion to an easily detectable substance.

Figure 6:
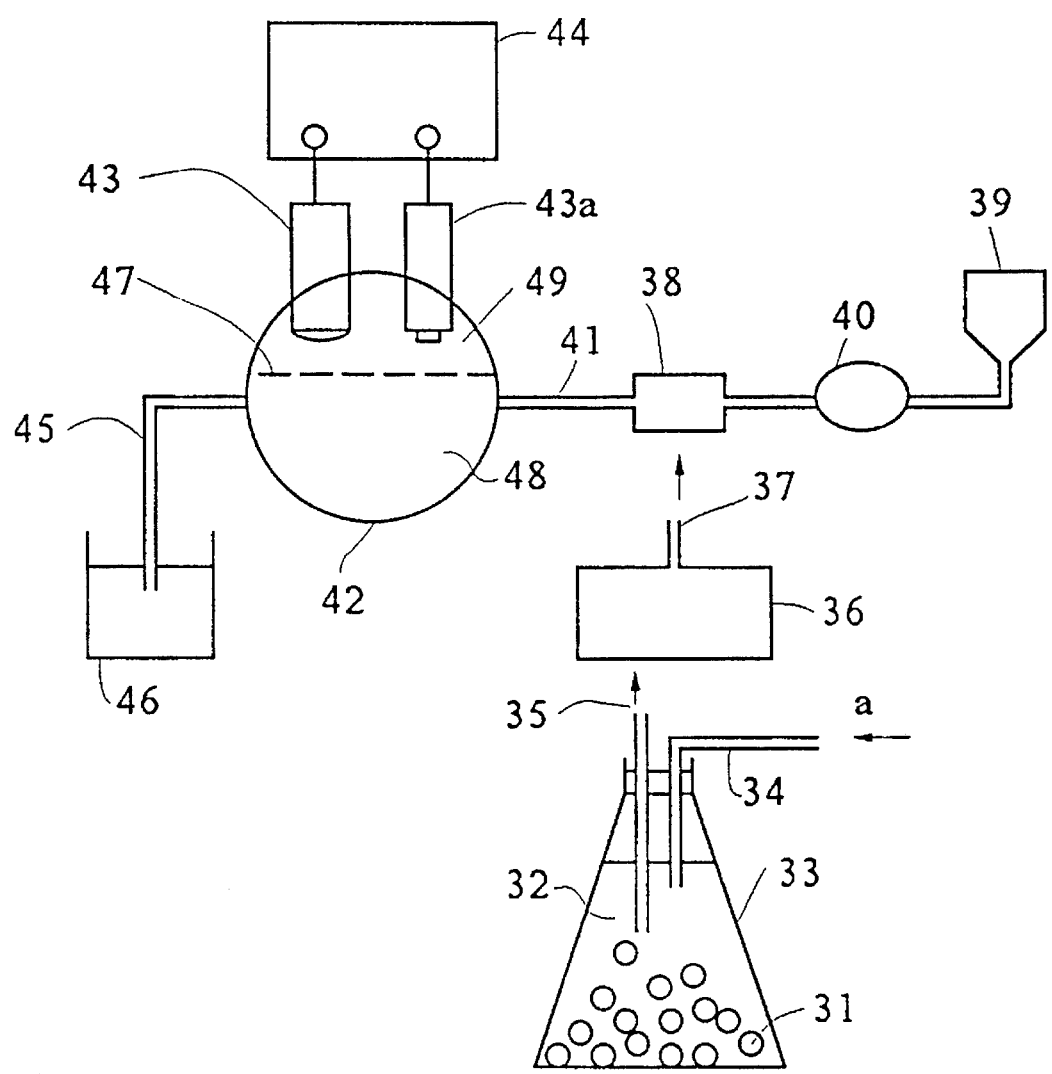
FIG. 6 schematically illustrates an example of an apparatus for carrying out an enzymatic reaction technique of a third embodiment of the present invention.

FIG. 6 schematically illustrates an example of an apparatus for a continuous process of a direct detection of ammonia in the above enzymatic technique. The apparatus mainly comprises a sample preparation system containing an enzymatic reaction chamber, etc.; an injecting system containing an injector, and a measuring system containing an ammonia electrode, etc.

When the detection of the leukocyte according to the first aspect of the present invention is carried out, a plurality of the sample preparation systems are preferably arranged, to prepare samples using the type I allergic and enzymatic reactions. A leukocyte sample 32 containing leukocytes 31 is charged into a reaction vessel 33, and a liquid containing a reference antigen (for example, a known allergen) is then added thereto from an inlet of a conduit 34 (shown by an arrow a in FIG. 6). Preferably, the reaction vessel 33 is allowed to stand in the presence of 1 to 10% carbon dioxide gas at 30° to 40° C. (particularly, 36° to 38 ° C.) for 1 to 3 hours, whereby the type I allergic reaction is carried out therein. After the reaction is completed, a reaction mixture, particularly a supernatant, is taken from a conduit 35. The reaction mixture is preferably centrifuged by a centrifuge (not shown), for example, at 100 to 1000 x g for 1 minute to 1 hour, to remove cells, and then fed to the enzymatic reaction chamber 36. An excess amount of diamineoxidase is added to the enzymatic reaction chamber 36, and a reaction is carried out therein at 28° to 33° C. for 10 minutes to 1 hour, depending upon a concentration of free histamine present therein. A sample of the resulting product is taken from a conduit 37, adjusted with sodium hydroxide or the like to a pH value which is the same as that of a buffer used in the measuring system, and fed to the measuring system by the injector 38.

The measuring system has been made stable by supplying a buffer from a buffer reservoir 39, by a pump 40, to the injector 38 and a flow cell 42. A buffer such as a phosphate buffer having a pH of 7 or more, preferably 10 or more, is used. A ratio of the sample from the enzymatic reaction chamber 36 to the buffer is not limited, but is preferably 5:1 to 1:10.

Figure 7:
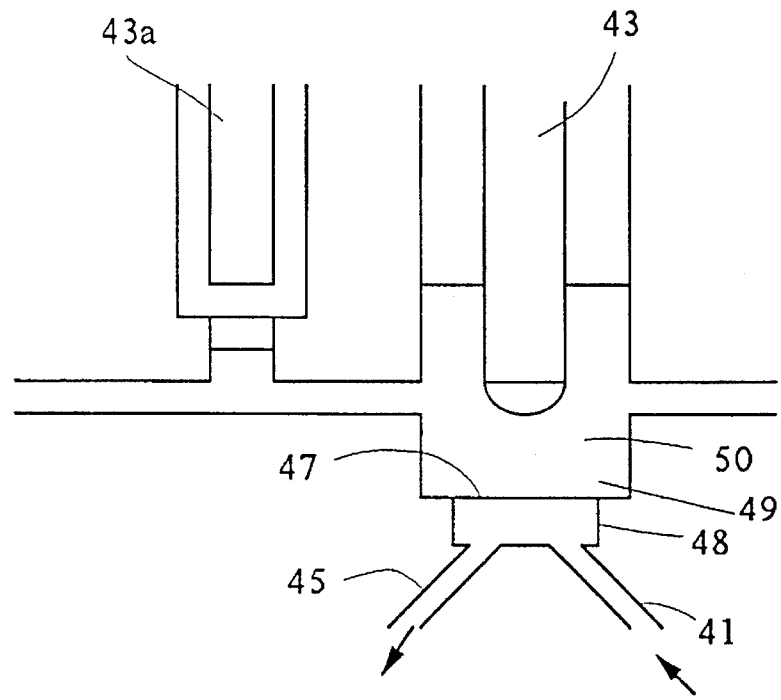
FIG. 7 is a sectional view schematically showing a measuring site in the apparatus of FIG. 6.

The sample is sent through the conduit 41 to the flow cell 42, and a concentration of ammonia therein is measured by the ammonia electrode 43, a reference electrode 43a, and a detector 44. The sample is then discharged through a conduit 45 to a drain bit 46. FIG. 7 illustrates an example of the measuring system containing the ammonia electrode or the like, in detail. As shown in FIG. 7, the flow cell 42 is divided by a barrier 47 into a sample chamber 48 and a detecting chamber 49. The barrier 47 is made of a material which permits gaseous ammonia, but does not permit water, liquid basic materials, or the like, to pass therethrough. As the material which permits the passage of gaseous ammonia, there may be mentioned cellulose acetate butyrate (containing 10 to 60 % by weight of a butylyl group and 5 to 30% by weight of an acetyl group), cellulose propionate valerate (containing 20 to 50% by weight of a valeryl group), acetylated cellulose acetate (containing 19% by weight or more of an acetyl group), polyethylene fluoride, or the like. The gaseous ammonia is fed from the sample chamber 48 via the barrier 47 to the detection chamber 49. A solution 50 of ammonium salt (for example, a solution of ammonium chloride) is filled in the detection chamber 49, and a liquid membrane type electrode 43 is dipped therein. A reference electrode 43a is immersed in a solution of various salts (for example, a solution of potassium chloride).

When the leukocytes in the liquid sample are not sensitized with a reference antigen, or are sensitized with an antigen other than the reference antigen added from the conduit 34, the generation of gaseous ammonia is not observed. Nevertheless, the generation of gaseous ammonia is observed, if an unknown antigen with which the leukocytes in the liquid sample are sensitized is identical to the known reference antigen added. Accordingly, it is possible to determine the kind of the antigen with which the leukocytes in the liquid sample are sensitized.

When an examination of one of the reference antigens is completed, the injection thereof is stopped, the system is washed by the buffer from the buffer reservoir 39, and then a liquid containing a next reference antigen is injected.

The detection of the antigen according to the second aspect of the present invention will be described.

Figure 8:
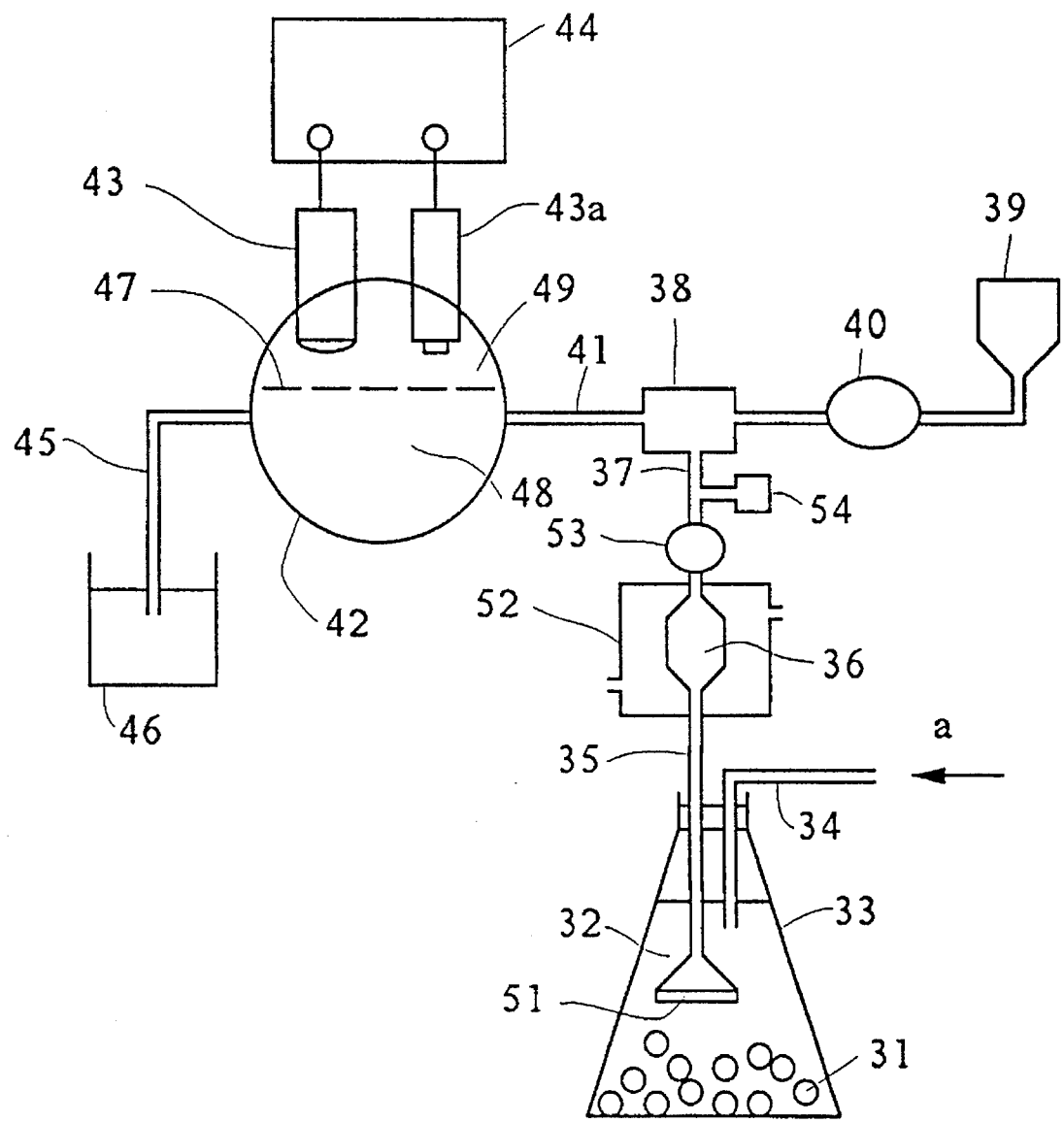
FIG. 8 schematically illustrates an example of an apparatus for carrying out in a continuous manner an enzymatic reaction technique of a third embodiment of the present invention.

FIG. 8 schematically illustrates an example of an apparatus suitable for a continuous process of a direct detection of ammonia in the above enzymatic technique. The apparatus mainly comprises a sample preparation system containing an enzymatic reaction chamber, etc.; and a measuring system containing an ammonia electrode, etc. In FIG. 8, devices which are the same as those shown in FIG. 6 are shown by the same reference numbers.

A plurality of the sample preparation systems are preferably arranged, to prepare samples using the type I allergic and enzymatic reactions. The sample preparation system mainly comprises a first reaction chamber containing sensitized reference leukocytes, wherein a type I allergic reaction is carried out; a means for injecting an antigen to the first reaction chamber; and a second reaction chamber wherein a deamination of histamine produced by the type I allergic reaction performed in the first reaction chamber is carried out in the presence of diamineoxidase. A liquid 32 containing sensitized reference leukocytes 31 is charged into a reaction vessel 33. Alternatively, the reference leukocytes may be immobilized on an appropriate support (for example, a membrane filter or a dialysis membrane having a pore size of 0.25 to 10 μm), and arranged in the reaction vessel 33. The immobilization can be carried out in the same way as in the above serotonin fluorescence technique.

Then, a liquid sample containing an unknown antigen (for example, an unknown allergen) is added from an inlet of a conduit 34 (shown by an arrow a in FIG. 8), and the reaction vessel 33 is preferably allowed to stand in the presence of 1 to 10% carbon dioxide gas at 30° to 40 ° C. (particularly, 36° to 38° C.) for 1 to 3 hours, whereby the type I allergic reaction is carried out therein. After the reaction is completed, a supernatant permeable through a membrane filter 51 in a reaction mixture is taken from a conduit 35, and then fed to the enzymatic reaction chamber 36.

The enzymatic reaction chamber 36 contains one or more columns which include immobilized diamineoxidase, and a heating device 52. The reaction is carried out in the reaction chamber 36 at 28° to 33° C. for 10 minutes to 1 hour, depending upon a concentration of free histamine present therein. A resulting reaction product is taken by a pump 53, a pH thereof is adjusted with a pH adjusting agent, such as a diluted sodium hydroxide, to prepare a sample, and the sample is fed to the measuring system via a conduit 37 and the injector 38. The subsequent procedures may be carried out as described above.

When an antigen capable of bonding to IgE antibodies on the sensitized reference leukocytes is not present in the liquid sample (antigen sample), the generation of gaseous ammonia is not observed. Nevertheless, the generation of gaseous ammonia is observed, if an antigen capable of bonding to IgE antibodies on the sensitized leukocytes is present in the liquid sample (antigen sample). An amount of generated gaseous ammonia is proportional to that of the antigen. As described above, it is possible to detect, in the liquid sample (antigen sample), the presence and absence of an antigen which is the same as the known antigen with which the reference leukocytes are sensitized.

When an examination of one of the antigen samples is completed, the injection thereof is stopped, the system is washed by the buffer from the buffer reservoir 39, and then a next antigen sample is injected.

Although the continuous process is described, this embodiment of the enzymatic reaction technique can be carried out batchwise. In the batch process, a sample prepared in the reaction chamber 36 is directly sent to the detection chamber 48 in the measuring system.

In addition to the technique using gaseous ammonia, hydrogen peroxide may be degraded by peroxidase in the presence of a dyestuff (an oxygen acceptor) such as otolidine or o-dianisidine, and a resulting oxidized dyestuff may be detected by colorimetry.

As explained above, according to the first aspect of the present invention, the kind of antigen with which leukocytes in a liquid sample are sensitized can be identified by a simple procedure which ensures a high accuracy and precise results, and without causing pain.

Further, according to the second aspect of the present invention, the presence of an antigen can be detected, and the kind thereof can be identified, by using sensitized reference leukocytes. Therefore, food which can be eaten by an allergic patient can be determined by a simple procedure which ensures a high accuracy and precise results, and without causing pain.

Examples

The present invention now will be further illustrated by, but is by no means limited to, the following Examples.

Example 1

The above first embodiment of the present invention was carried out, using an apparatus as shown in FIGS. 1 and 2.

Blood was drawn from a patient (5 years and 2 months old; male) suffering from atopic dermatitis, and immediately thereafter, a 2% methylcellulose solution was added thereto. The whole was then allowed to stand at a room temperature for 40 minutes, whereby an erythrocyte sedimentation was effected. Thereafter, a supernatant was taken and centrifuged (150 x g, 5 minutes) to obtain leukocytes as a precipitate, and after washing, the leukocytes were resuspended in a PBS (phosphate buffered saline) (pH 7.4), while adjusting the number of cells to $5 \times 10^5$ cells/ml. Using the resuspension and a membrane filter (pore size: 0.45 μm), leukocytes were immobilized on a surface (19.6 mm$^2$) of a BPG (basalplane pyrolytic graphite) electrode, to thus prepare a working electrode. A platinum wire was used as a counter electrode and an SCE was used as a reference electrode, and a cyclic voltametry was carried out in a PBS (pH 7.4) at a scanning rate of 10 mV/sec. A peak current of 0.65 μA/10$^6$ cells was observed at 0.30 V. to 0.34 V.vs.SCE.

Albumen (the white of a hen's egg) and cow's milk were added to a PBS (pH 7.4) in an amount of 100 μg/ml (calculated in terms of protein), respectively. When the PBS containing milk was added, a peak current of 0.64 μA/10$^6$ cells was obtained at 0.30 V. to 0.34 V.vs.SCE, and when the PBS containing albumen was added, a peak current of 0.45 μA/10$^6$ cells was obtained at 0.30 V. to 0.34 V.vs.SCE, i.e., a drop occurred in the peak current. The result proved that the patient was allergic to hen's eggs.

Example 2

Blood was drawn from a patient (43 years old; male) suffering from pollinosis, and leukocytes were obtained therefrom as in Example 1. An apparatus similar to that used in Example 1 and containing a BPG as a working electrode, a platinum wire as a counter electrode, and an SSCE as a reference electrode was used. The leukocytes were brought into contact with the working electrode by a membrane filter, and a differential pulse voltammetry was carried out under the conditions of a scanning potential of 0 to 1.0 V(vs.SSCE), a sampling time of 20 ms, a modulation voltage of 50 mV and 10 mV, and a potential sweep of 0.5 mV/s. A Polarograph model-321 (Fuso Seisakusyo) was used as the measuring apparatus. A peak current (as a differential current) of 0.70μA/10$^6$ cells was obtained at 0.30 to 0.34 V. vs. SSCE.

Pollen of a Japanese cedar (sugi), ragweed, a Japanese cypress (hinoki) or a rice plant was added to a PBS (pH 7.4), respectively. When the PBS containing the pollen of a Japanese cedar (sugi) was added, a peak current of 0.56 μA/10$^6$ cells was obtained, but no drop of the peak current was observed when other pollens were added to the PBS. The result proved that the patient was allergic to the pollen of a Japanese cedar (sugi).

Example 3

The serotonin electrode method was carried out, using an apparatus as shown in FIG. 4. Platinum wires were used as a working electrode and a counter electrode, respectively, and an SCE was used as a reference electrode. A constant voltage of 0.3 V.vs.SCE was applied to the working electrode, and a rate of a mobile phase in a flow system was 0.4 ml/min.

Figure 9:
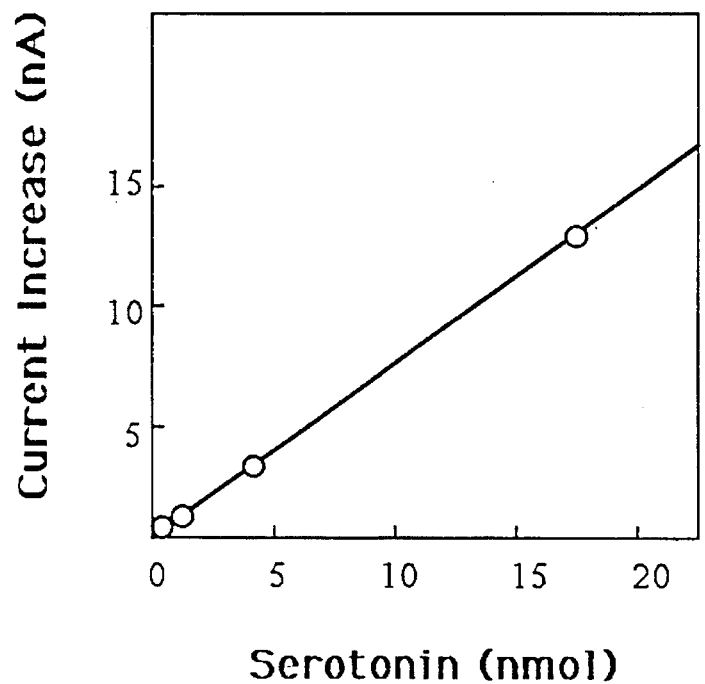
FIG. 9 is a graph showing a relationship between an amount of serotonin and a current increase.

Before leukocytes in a liquid sample were immobilized on a membrane 15a, a preliminary test was carried out wherein a PBS (0.1 ml) containing 5, 10, 40 or 170 μM serotonin was added from the injector 16, and the relationship between an amount of serotonin and a current increase was observed. The result is shown in FIG. 9.

Then, four blood samples were drawn from four persons, i.e., person A (suffering from atopic dermatitis; 5 years old; male), person B (suffering from pollinosis; 39 years old; male), person C (normal; 27 years old; male), and person D (normal; 56 years old; male), and immediately thereafter, a 2% methylcellulose solution was added thereto. The whole was then allowed to stand at a room temperature for 40 minutes, whereby an erythrocyte sedimentation was effected. Thereafter a supernatant was taken and centrifuged (150 x g, 5 minutes) to obtain leukocytes as a precipitate, and after washing, the leukocytes were resuspended in a PBS (phosphate buffered saline) (pH 7.4), while adjusting the number of cells to 5×10⁵ cells/ml. The resuspension (2 ml) of leukocytes was fed from the injector 16, and leukocytes were immobilized on a carrier 15a (a membrane filter having a pore size of 5 μm).

Thereafter, solutions (2 ml, each) of various extracts of known allergens (3 μg/ml; calculated in terms of protein) were fed from the injector 16, respectively, and a current value was measured. The known allergens used were a hen's egg, cow's milk, a soybean, pollen of a Japanese cedar (sugi), and pollen of ragweed. The extraction was effected by using a PBS. The results are shown in Table 1.

TABLE I

| Allergen | Egg | Milk | Soybean | Cedar | Ragweed |
|---|---|---|---|---|---|
| Person A | 2.0 | 0.2 | 0.0 | 0.0 | 0.0 |
| Person B | 0.1 | 0.0 | 0.0 | 2.3 | 0.3 |
| Person C | 0.2 | 0.1 | 0.1 | 0.0 | 0.0 |
| Person D | 0.0 | 0.0 | 0.0 | 0.2 | 0.2 |

(The unit in TABLE 1 is nA.)

As apparent from Table 1, it was determined that the person A is allergic to eggs, the person B is allergic to the pollen of a Japanese cedar, and that the persons C and D are not allergic to the above allergens.

Example 4

The serotonin fluorescence method was carried out, using an apparatus as shown in FIG. 5. A Fluorescence-spectrophtometer F-1200 (Hitachi, Ltd.) was used as a fluorescence-photometer. An exciting wave length was applied at 298 nm, a fluorescence at 330 nm was detected, and a rate of a mobile phase was 0.4 ml/min.

Figure 10:
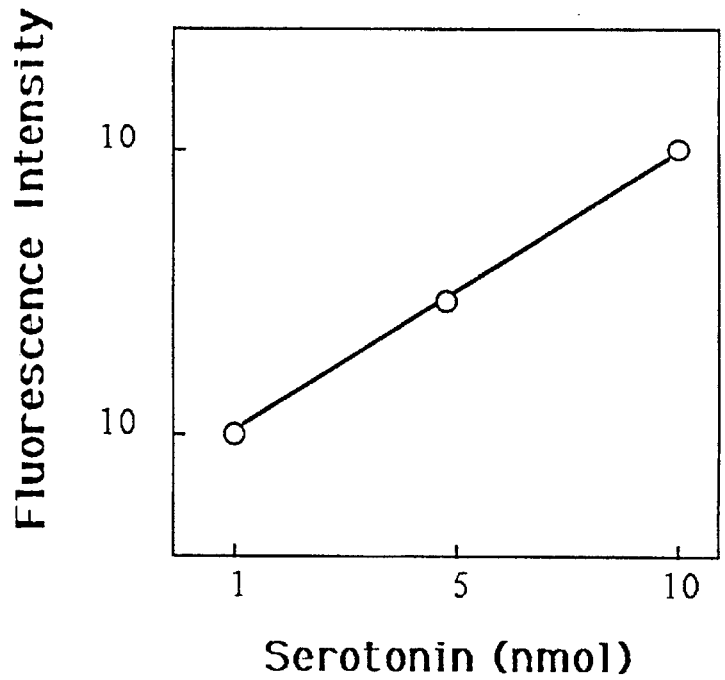
FIG. 10 is a graph showing a relationship between an amount of serotonin and a fluorescence intensity.

Before leukocytes in a liquid sample were immobilized on a membrane 22a, a preliminary test was carried out wherein a PBS (0.1 ml) containing 10, 50 or 100 μM serotonin was added from the injector 21, and the relationship between an amount of serotonin and an increase of the fluorescence was observed. The result is shown in FIG. 10.

Then, four blood samples were drawn from four persons, i.e., the person A (suffering from atopic dermatitis; 5 years old; male), the person B (suffering from pollinosis; 39 years old; male), the person C (normal; 27 years old; male), and the person D (normal; 56 years old; male), and immediately thereafter, a 2% methylcellulose solution was added thereto. The whole was then allowed to stand at a room temperature for 40 minutes, whereby an erythrocyte sedimentation was effected. Thereafter, a supernatant was taken and centrifuged (150 x g, 5 minutes) to obtain leukocytes as a precipitate, and after washing, the leukocytes were resuspended in a PBS (phosphate buffered saline) (pH 7.4), while adjusting the number of cells to 5× 10⁵ cells/ml. The resuspension (2 ml) of leukocytes was fed from the injector 21, and leukocytes were immobilized on a carrier 22a (a membrane filter having a pore size of 5 μm).

Thereafter, solutions (2 ml, each) of various extracts of known allergens (3 μg/ml; calculated in terms of protein) were fed from the injector 21, respectively, and a current value was measured. The known allergens used were a hen's egg, cow's milk, a soybean, pollen of a Japanese cedar (sugi), and pollen of ragweed. The extraction was effected by using a PBS. The results are shown in Table 2.

TABLE 2

| Allergen | Egg | Milk | Soybean | Cedar | Ragweed |
|---|---|---|---|---|---|
| Person A | 1.2 × 10⁴ | 1.0 × 10³ | — | — | — |
| Person B | 3.7 × 10² | — | — | 1.3 × 10⁴ | 3.5 × 10³ |
| Person C | 1.1 × 10³ | 5.9 × 10² | 2.2 × 10² | — | — |
| Person D | — | — | — | — | 2.0 × 10³ |

(The numerical value in TABLE 2 is a fluorescence intensity, and "—" means undetectable.)

As apparent from Table 2, it was determined that the person A is allergic to eggs, the person B is allergic to the pollen of a Japanese cedar, and that the persons C and D are not allergic to the above allergens.

Example 5

The enzymatic method was carried out, using an apparatus as shown in FIGS. 6 and 7. Here, a 10 mM ammonium chloride solution as an internal solution contained in the detection chamber 49, and a 3.3 M potassium chloride solution as a solution in which the reference electrode 43a was immersed were used, and a rate of a mobile phase was 0.4 ml/min.

Figure 11:
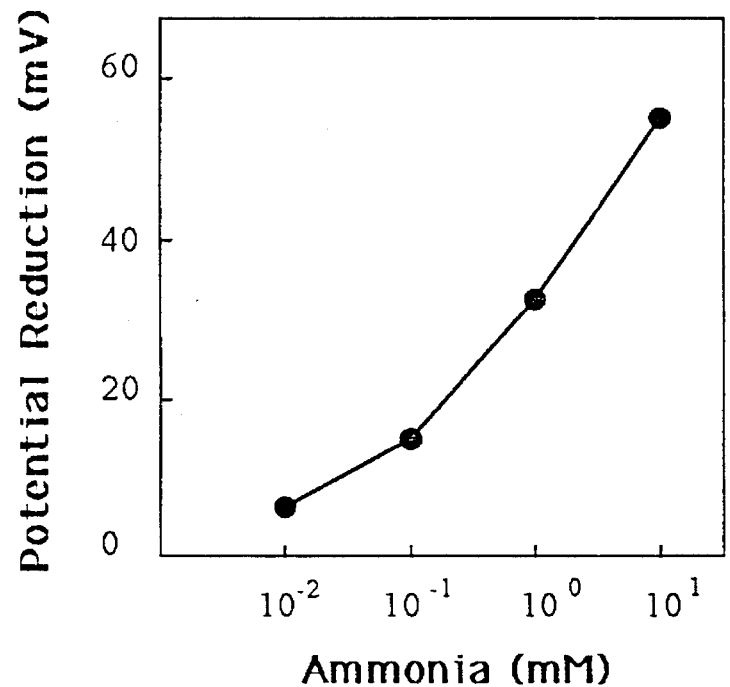
FIG. 11 is a graph showing a relationship between a concentration of ammonia and a potential reduction.

Before leukocytes in a liquid sample were charged into the reaction vessel 33, two kinds of preliminary tests were carried out wherein phosphate buffers (pH 11) (0.5 ml) containing 1×10², 1×10¹, 1, and 10 mM ammonium ions were fed from the injector 38, and the potential reduction at the ammonia electrode was observed. The result is shown in FIG. 11.

Figure 12:
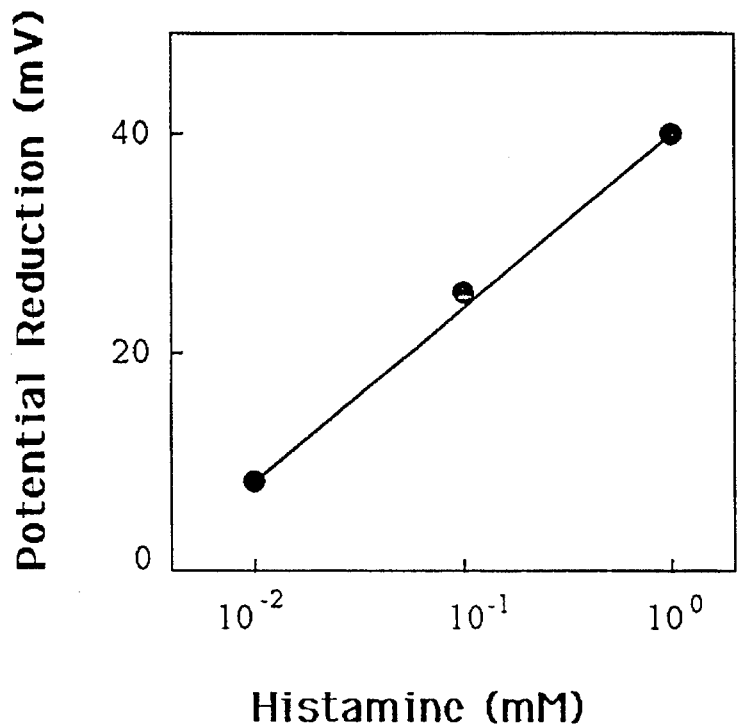
FIG. 12 is a graph showing a relationship between a concentration of histamine and a potential reduction.

Further, a PBS (pH 7.4) (2 ml) containing 1×10², 1×10¹, or 1 mM histamine, and diamineoxidase (Si Chemical Corp.) (0.2 unit) were added to the enzymatic reaction chamber 36, and after the reaction was carried out at 30 ° C. for 30 minutes, the pH thereof was adjusted to 11 by the addition of a sodium hydroxide solution. The resulting sample (0.5 ml) was fed from the injector 38 to the measuring system, and the relationship between a concentration of histamine and a voltage reduction at the ammonia electrode was observed. The result is shown in FIG. 12.

Then, four blood samples were drawn from four persons, i.e., the person A (suffering from atopic dermatitis; 5 years old; male), the person B (suffering from pollinosis; 39 years old; male), the person C (normal; 27 years old; male), and the person D (normal; 56 years old; male), and immediately thereafter, a 2% methylcellulose solution was added thereto. The whole was then allowed to stand at 27° C. for 40 minutes, whereby an erythrocyte sedimentation was effected. Thereafter, a supernatant was taken and centrifuged (150 x g, 5 minutes), to obtain leukocytes as a precipitate, and after washing, the leukocytes were resuspended in a PBS (phosphate buffered saline) (pH 7.4), while adjusting the number of cells to 5×10⁵ cells/mi. The resuspension (2 ml) of leukocytes was then fed to the reaction chamber 33.

Thereafter, solutions (1 ml, each) of various extracts of known allergens (3 μg/ml; calculated in terms of protein) were added, respectively, and mildly stirred at 37 ° C. for 5 minutes. The resulting mixture was centrifuged (150 x g, 5 minutes), and the supernatant was taken and poured into the enzymatic reaction chamber 36.

Further, diamineoxidase was added thereto in an amount of 0.05 unit/ml and a reaction was carried out at 30° C. for 30 minutes, and after the reaction was completed, the pH thereof was adjusted to 11 by a sodium hydroxide solution.

The resulting sample (0.5 ml) was fed to the measuring system from the injector 38, and a concentration of ammonium ions therein was measured. The known allergens used were a hen's egg, cow's milk, a soybean, pollen of a Japanese cedar (sugi), and pollen of ragweed. The extraction was effected by using a PBS. The results are shown in Table 3.

TABLE 3

| Allergen | Egg | Milk | Soybean | Cedar | Ragweed |
| --- | --- | --- | --- | --- | --- |
| Person A | 14 | 5 | 3 | 2 | 3 |
| Person B | 3 | 4 | 3 | 16 | 4 |
| Person C | 5 | 4 | 5 | 2 | 5 |
| Person D | 5 | 5 | 4 | 3 | 5 |

(The unit in TABLE 3 is mV.)

As apparent from Table 3, it was determined that the person A is allergic to eggs, the person B is allergic to the pollen of a Japanese cedar, and that the persons C and D are not allergic to the above allergens.

Example 6

The above first embodiment of the present invention was carried out, using an apparatus as shown in FIG. 1.

Blood was drawn from a patient (7 years old; female) suffering from atopic dermatitis, and immediately thereafter, a 2% methylcellulose solution was added thereto. The whole was then allowed to stand at a room temperature for 40 minutes, whereby an erythrocyte sedimentation was effected. Thereafter, a supernatant was taken and centrifuged (150 x g, 5 minutes) to obtain the leukocytes as a precipitate, and after washing, the leukocytes were resuspended in a PBS, while adjusting the number of cells to $5 \times 10^5$ cells/mi. Using the resuspension and a membrane filter (pore size: 0.45 μm), the leukocytes were immobilized on a surface (19.6 mm$^2$) of a BPG (basalplane pyrolytic graphite) electrode, to prepare a working electrode. A platinum wire was used as a counter electrode, an SCE was used as a reference electrode, and a cyclic voltammetry was carried out in a PBS (pH 7.4) at a scanning rate of 10 mV/sec. A peak current of 0.67 μA/10$^6$ cells was observed at 0.34 V.vs.SCE.

Thereafter, non-soybean soy sauce (shoju) (Daizunon: Shinshin Kaken Co., Ltd.) was added in an amount of 1 mg/ml, and thus a peak current of 0.64 μA/10$^6$ cells was obtained at 0.34 V.vs.SCE. When a usual soy sauce was added, a peak current of 0.30 μA/10$^6$ cells was obtained at 0.34 V.vs.SCE. Therefore, it can be assumed that the intake of the above non-soybean soy sauce ("Daizunon") does not cause the atopic dermatitis of the patient.

Peroral elimination and feed tests were performed on the patient using "Daizunon" and a usual soy sauce, and as a result, it was found that Daizunon did not cause the allergy. On the other hand, the patient complained of an itch in the mouth 4 minutes after an intake of the usual soy sauce, and a rash was observed over the whole body of the patient 2 hours after this intake. Therefore, it is apparent that the result of the detection according to the present invention is consistent with an actual allergy.

Example 7

Using an apparatus as shown in FIG. 1, the procedure as set forth in Example 6 was repeated, except that RBL-1 (rat basophlic leukemia; commercially available from Seikagaku Kogyo Co., Ltd.) was used. RBL-1 cells were suspended in tris ACM (tris containing albumin from bovine serum, calcium chloride and magnesium) (pH 7.6), while adjusting the number of cells.

Blood was drawn from a patient suffering from atopic dermatitis (the patient of Example 6; 7 years old; female), and immediately thereafter, heparin (20 units/ml) and then a 2% methylcellulose solution (5 ml) were added thereto. The whole was then allowed to stand at a room temperature for 40 minutes, whereby an erythrocyte sedimentation was effected. A supernatant was taken to obtain an antiserum containing IgE antibodies.

The resulting antiserum (2 ml) was added to 2 ml of the suspension of the RBL-1 cells (10$^6$ cells/ml), and the whole was allowed to stand at 37° C. for 2 hours in the presence of 5% carbon dioxide gas, to sensitize the RBL-1 cells with the IgE antibodies.

Using a suspension (2 ml) of the resulting sensitized RBL-1 cells (10$^5$ cells/ml) and a membrane filter (pore size: 0.45 μm), the sensitized leukocytes were brought into contact with and immobilized on a surface (19.6 mm$^2$) of a BPG (basalplane pyrolytic graphite) electrode, to prepare a working electrode. A platinum wire was used as a counter electrode, an SCE was used as a reference electrode, and a cyclic voltammetry was carried out in a PBS (pH 7.4) at a scanning rate of 10 mV/sec. A peak current of 0.62 μLA/10$^6$ cells was observed at 0.34 V.vs.SCE.

Thereafter, non-soybean soy sauce (shoyu) (Daizunon: Shinshin Kaken Co., Ltd.) was added in an amount of 1 mg/ml, and thus a peak current of 0.60 μA/10$^6$ cells was obtained at 0.34 V.vs.SCE. When a usual soy sauce was added, a peak current of 0.30/10$^6$ cells was obtained at 0.34 V.vs.SCE. Therefore, it can be assumed that the intake of the above non-soybean soy sauce ("Daizunon") does not cause the atopic dermatitis of the patient.

Example 8

The serotonin electrode method was carried out, using an apparatus as shown in FIG. 4. Platinum wires were used as a working electrode and a counter electrode, respectively, and an SCE was used as a reference electrode. A constant voltage of 0.3 V.vs.SCE was applied to the working electrode, and a rate of a mobile phase in a flow system was 0.4 ml/min.

Blood was drawn from a patient (5 years old; male) suffering from atopic dermatitis caused by an allergy to hen's eggs, and leukocytes were obtained as in Example 6. After washing, the leukocytes were resuspended in a PBS (pH 7.4), while adjusting the number of cells to $5 \times 10^5$ cells/mi. The resulting suspension (2 ml) containing leukocytes was fed from the injector 16, and the leukocytes were immobilized on the membrane 15a (a membrane filter having a pore size of 5 μm).

Thereafter, allergens were extracted with a PBS from a biscuit prepared for an allergic patient (Raisin Cookie; Nichieido) and from a usual cookie, respectively, to prepare liquid samples containing allergen extracts in an amount of 3 μg/ml (calculated in terms of protein), the resulting liquid samples were fed from the injector 16, and the current values were measured.

As a result, a current value of 0.2 nA was obtained for the liquid sample containing the extract of the biscuit prepared for an allergic patient ("Raisin Cookie"), whereas 1.9 nA was obtained for the liquid sample containing the extract of the usual biscuit. Therefore, it was safe to assume that the "Raisin Cookie" did not contain the allergen for the patient, and when the patient actually ate the "Raisin Cookie", no allergic reaction was observed.

Example 9

The serotonin electrode method was carried out, using an apparatus as shown in FIG. 4. Platinum wires were used as a working electrode and a counter electrode, respectively, and an SCE was used as a reference electrode. A constant voltage of 0.3 V.vs.SCE was applied to the working electrode, and a rate of a mobile phase in a flow system was 0.4 ml/min.

As cultivated basophils from an animal, RBL-1 (rat basophlic leukemia; Seikagaku Kogyo Co., Ltd.) was used, and RBL-1 cells were suspended in tris ACM (pH 7.6), while adjusting the number of cells.

Blood (40 ml) was drawn from the patient (5 years old; male) allergic to hen's eggs, and immediately thereafter, heparin (20 units/ml) and then, a 2% methylcellulose solution (5 ml) were added thereto. The whole was then allowed to stand at 27 ° C. for 30 minutes, whereby an erythrocyte sedimentation was effected. A supernatant was then obtained as an antiserum containing IgE antibodies.

The resulting antiserum (2 ml) was added to 2 ml of the suspension of the RBL-1 cells, and the whole was allowed to stand at 37 ° C. for 2 hours in the presence of 5% carbon dioxide gas, to sensitize the RBL-1 cells with the IgE antibodies.

A suspension (0.4 ml) of the resulting sensitized RBL-1 cells was supported on the membrane 15a (a membrane filter having a pore size of 5 µm).

Thereafter, allergens were extracted with a PBS from a bread prepared for an allergic patient (Table Roll; Nichieido) and from a usual bread (table roll), respectively, to prepare liquid samples containing allergen extracts in an amount of 3 µg/ml (calculated in terms of protein), and the resulting liquid samples were fed from the injector 16, and the current values were measured.

As a result, a current value of 0.1 nA was obtained for the liquid sample containing the extract of the bread prepared for an allergic patient ("Table Roll"), whereas 1.8 nA was obtained for the liquid sample containing the extract of the usual table roll. Therefore, it was safe to assume that the "Table roll" did not contain the allergen for the patient, and when the patient actually ate the "Table Roll", no allergic reaction was observed.

Example 10

The serotonin fluorescence method was carried out, using an apparatus as shown in FIG. 5. A Fluorescence-spectrophtometer F-1200 (Hitachi, Ltd.) was used as a fluorescence-photometer. An exciting wave length was applied at 298 nm, a fluorescence at 330 nm was detected, and a rate of a mobile phase was 0.4 ml/min.

Sensitized leukocytes were prepared by collecting leukocytes from 5 patients allergic to cow's milk, as in Example 6, and diluted in the same ratio as in Example 6.

The resulting suspension (2 ml) containing sensitized leukocytes ($5 \times 10^5$ cells/ml) was fed from the injector 21 and the sensitized leukocytes were immobilized on the membrane 22a (a membrane filter having a pore size of 5 µm).

Thereafter, allergens were extracted with a PBS from milk digested by enzymes (MA-1; Morinaga Milk K. K.) and from a usual milk, respectively, to prepare liquid samples containing allergen extracts in an amount of 3 µg/ml (calculated in terms of protein), the resulting liquid samples were fed from the injector 21, and a fluorescence (330 nm) emitted by applying an exciting wave length (298 nm) was measured.

As a result, a fluorescence intensity of $1.0 \times 10^3$ was obtain for the liquid sample containing the extract of the milk digested by enzymes (MA-1), whereas a fluorescence intensity of $1.8 \times 10^4$ was obtained for the liquid sample containing the extract of the usual milk. Therefore, it is apparent that the the milk digested by enzymes (MA-1) is effective for a patient having an allergy to cow's milk.

Example 11

The procedure as set forth in Example 10 was repeated, except that sensitized RBL-1 cells were used.

RBL-1 cells were suspended in tris ACM (pH 7.6), while adjusting the number of cells to $10^6$ cells/ml.

Blood was taken from the five patients having an allergy to cow's milk (the same patients as in Example 10), and an antiserum was prepared by diluting as in Example 7.

The resulting antiserum (2 ml) was added to 2 ml of the suspension (2 ml) of the RBL-1 cells ($10^6$ cells/ml), and the whole was then allowed to stand at 37° C. for 2 hours in the presence of 5% carbon dioxide gas, to sensitize the RBL-1 cells with the IgE antibodies.

A suspension (2 ml) of the resulting sensitized RBL-1 cells ($10^5$ cells/ml) was supported on the membrane 22a (a membrane filter having a pore size of 5 µm).

Thereafter, allergens were extracted with a PBS from milk digested by enzymes (MA-1; Morinaga Milk K. K.) and from a usual milk, respectively, to prepare liquid samples containing allergen extracts in an amount of 3 µg/ml (calculated in terms of protein), the resulting liquid samples were fed from the injector 21, and a fluorescence (330 nm) emitted by applying an exciting wave length (298 nm) was measured.

As a result, a fluorescence intensity of $9.8 \times 10^2$ was obtain for the liquid sample containing the extract of the milk digested by enzymes (MA-1), whereas a fluorescence intensity of $1.6 \times 10^4$ was obtained for the liquid sample containing the extract of the usual milk. Therefore, it is apparent that the the milk digested by enzymes (MA-1) is effective for a patient having allergy to cow's milk.

Further, the result of this Example 11 is consistent with that of Example 10.

Example 12

The enzymatic method was carried out, using an apparatus as shown in FIG. 8. A phosphate buffer (pH 11) was used as a buffer in the reservoir 39 for the measuring system, a 10 mM ammonium chloride solution as an internal solution in the detection chamber 49, and a 3.3 M potassium chloride solution as a solution in which the reference electrode 43a was immersed. The flow rates in the enzymatic reaction system and the measuring system of the ammonia electrode were 0.5 ml/min, respectively.

Blood (40 ml) was drawn from a patient (39 years old; male) having pollinosis caused by the pollen of a Japanese cedar (sugi), and immediately thereafter, heparin (20 units/ml) and then, a 2% methylcellulose solution (5 ml) were added thereto. The whole was then allowed to stand at 27° C. for 40 minutes, and a supernatant was centrifuged (150 x g, 5 minutes) to obtain leukocytes as a precipitate. After washing, the leukocytes were resuspended in a PBS, while adjusting the number of cells to $5\times10^5$ cells/ml. The resuspension was then charged into the reaction vessel 33.

Figure 13:
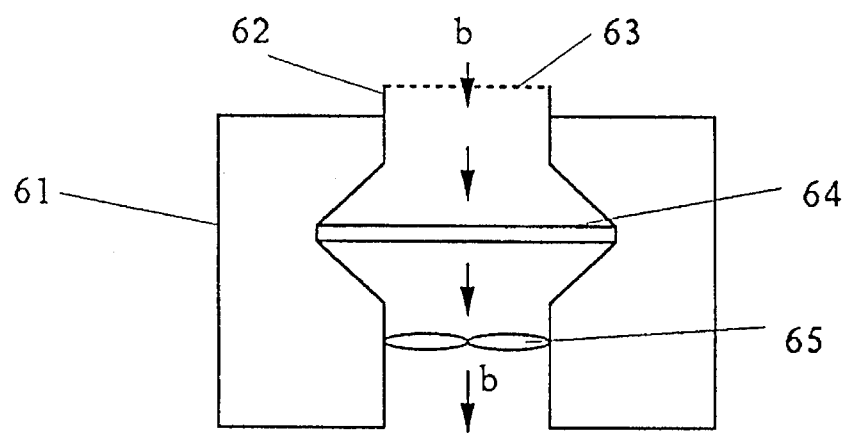
FIG. 13 is a sectional view of a collecting device of suspended particles.

Particles suspended in the air were used as an antigen sample, and the suspended particles were collected by a collecting device 61 as shown in FIG. 13, in Koganei city, Tokyo, for 10 hours on Mar. 2, 1989. The collecting device 61 has a first filter 63 (pore size: 1 mm) at an intake vent 62 and a second filter 64 (pore size: 5 μm) in the center thereof. The suspended particles were collected by rotating a fan 65 disposed inside of the filters to produce an air flow (shown by an arrow a in FIG. 13) at a rate of about 10 m3/min, and the particles were extracted with a PBS in an amount of 3 μg/ml (calculated in terms of protein), to prepare the unknown antigen sample.

The enzymatic reaction chamber 36 contained diaminoxidase (0.1 unit) immobilized on silica particles, and the temperature of the reaction chamber 36 was maintained at 30° C. with warm water supplied by a heating device 52. As a pH adjusting agent, a 5 % aqueous sodium hydroxide solution was stored in the reservoir 54.

When the suspension (2 ml) containing the leukocytes was charged in the reaction vessel 33, a voltage of 5 mV was obtained. Subsequently, the allergen extract liquid sample (0.5 ml) was added to the reaction vessel 33, and a voltage of 14 mV was obtained. This result shows that the pollen of a Japanese cedar (sugi) was suspended in the air.

Example 13

The procedure as set forth in Example 12 was repeated, except that sensitized RBL-1 cells were used.

RBL-1 cells were suspended in tris ACM (pH 7.6), while adjusting the number of cells to $10^6$ cells/ml.

Blood was obtained from the patient (39 years old; male) having pollinosis caused by the pollen of a Japanese cedar (sugi) (the same patient as in Example 12), and an antiserum was prepared by diluting as in Example 7.

The resulting antiserum (2 ml) was added to 2 ml of the suspension (2 ml) of the RBL-1 cells ($10^6$ cells/ml), and the whole was then allowed to stand at 37° C. for 2 hours in the presence of 5% carbon dioxide gas, to sensitize the RBL-1 cells with the IgE antibodies.

As an antigen sample, suspended particles prepared as in Example 12 were used. When the suspension (2 ml) containing the sensitized RBL-1 ($5\times10^5$ cells/ml) was charged in the reaction vessel 33 of the apparatus as shown in FIG. 8, a voltage of 4 mV was obtained. Subsequently, the allergen extract liquid sample (0.5 ml) was added to the reaction vessel 33, and a voltage of 12 mV was obtained. This result shows that the pollen of a Japanese cedar (sugi) was suspended in the air. Further, the result of this Example 13 is consistent with that of Example 12.

Although the present invention has been described with reference to specific embodiments, various changes and modifications obvious to those skilled in the art are deemed to be within the spirit, scope and concept of the invention.

I claim:

1. A process for detecting in a liquid sample containing at least 100 leukocytes, said leukocytes containing all hemocytes present in whole blood other than erythrocytes and hemocytes a leukocyte sensitized with an antigen capable of participating in a type I allergic reaction and which causes atopic dermatitis or pollinosis, comprising the steps of:

(A) adding to said liquid sample a known antigen capable of participating in a known type I allergic reaction;

(B) applying to said liquid sample from step (A) an exciting wave of 293 to 303 nm; and (C) detecting fluorescence at 325 to 335 nm to thereby detect serotonin released during said known type I allergic reaction.

2. A process for detecting, in a liquid sample containing food or pollen, an antigen capable of participating in a type I allergic reaction and which causes atopic dermatitis or pollinosis, comprising the steps of:

(A) adding to said liquid sample, human leukocytes sensitized with a known antigen capable of participating in a known type I allergic reaction.., said leukocytes containing at least 100 hemocytes present in whole blood other than erythrocytes and platelets;

(B) applying an exciting wave of 293 to 303 nm; and (C) detecting a fluorescence at 325 to 335 nm to thereby detect serotonin released by said known type I allergic reaction.

3. An apparatus for detecting an antigen capable of participating in a type I allergic reaction and which causes atopic dermatitis or pollinosis comprising:

(A) a reaction chamber comprising a membrane support having supported thereon at least 100 human leukocytes, said leukocytes containing all hemocytes present in whole blood other than erythrocytes and platelets;

(B) means for injecting liquid into said reaction chamber; and (C) means for detecting fluorescence of serotonin released during a type I allergic reaction which occurs in said reaction chamber, wherein detection of fluorescence correlates with the presence in the reaction chamber of an antigen capable of participating in a type I allergic reaction with said leukocytes.

4. The apparatus as set forth in claim 3 wherein said human leukocytes are obtained from a blood sample of a single person and said liquid contains a known antigen.

5. The apparatus as set forth in claim 3 wherein said human leukocytes are sensitized with at least one known antigen and said liquid contains a sample of pollen or food.

* * * * *

UNITED STATES PATENT AND TRADEMARK OFFICE
CERTIFICATE OF CORRECTION

PATENT NO. : 5,476,797
DATED : December 19, 1995
INVENTOR(S) : Tadashi Matsunaga It is certified that error appears in the above-indentified patent and that said Letters Patent is hereby corrected as shown below:

On the title page,

Item [73] Assignee:

After "Asahi Denka Kogyo K.K., Tokyo, Japan" add --(a part interest) --.

Signed and Sealed this

Twenty-fifth Day of June, 1996

Attest:

BRUCE LEHMAN

*Attesting Officer*   *Commissioner of Patents and Trademarks*